United States Patent
Yagi et al.

(10) Patent No.: US 6,429,220 B1
(45) Date of Patent: Aug. 6, 2002

(54) ANTIBACTERIAL COMPOSITIONS

(75) Inventors: Minoru Yagi, Hiratsuka; Urara Usui, Aikoh-Gun, both of (JP)

(73) Assignee: Kurita Water Industries Ltd., Tokyo (JP)

( * ) Notice: Subject to any disclaimer, the term of this patent is extended or adjusted under 35 U.S.C. 154(b) by 0 days.

(21) Appl. No.: 09/786,291

(22) PCT Filed: Aug. 31, 1999

(86) PCT No.: PCT/JP99/04727

§ 371 (c)(1),
(2), (4) Date: Mar. 1, 2001

(87) PCT Pub. No.: WO00/13510

PCT Pub. Date: Mar. 16, 2000

(30) Foreign Application Priority Data

Sep. 3, 1998 (JP) ............................................ 10-249736
Aug. 17, 1999 (JP) ............................................ 11-230876

(51) Int. Cl.[7] ..................... A01N 43/80; A01N 25/00; A61K 31/425
(52) U.S. Cl. .................................... 514/372; 424/405
(58) Field of Search ........................... 514/372; 424/405

(56) References Cited

U.S. PATENT DOCUMENTS

| | | | |
|---|---|---|---|
| 3,415,655 A | * 12/1968 | Hino et al. ................... | 99/54 |
| 3,870,795 A | 3/1975 | Miller et al. | |
| 4,150,026 A | 4/1979 | Miller et al. | |
| 4,824,957 A | 4/1989 | Amick | |
| 4,980,176 A | 12/1990 | Berke et al. | |
| 5,160,666 A | 11/1992 | Lindner et al. | |
| 5,217,711 A | * 6/1993 | DeOliveira ................... | 424/70 |
| 5,342,836 A | 8/1994 | Reeve | |

FOREIGN PATENT DOCUMENTS

| | | | |
|---|---|---|---|
| EP | 0 166 611 | | 1/1986 |
| EP | 236119 | | 9/1987 |
| EP | 0 425 143 A | | 5/1991 |
| JP | 54-23968 | | 8/1979 |
| JP | 61-56174 | | 3/1986 |
| JP | 61-212576 | | 9/1986 |
| JP | 62-252708 A | | 11/1987 |
| JP | 5-124917 | | 5/1993 |
| JP | 5-246807 | | 9/1993 |
| JP | 08214775 | * | 8/1996 |
| JP | 9-263504 A | | 10/1997 |
| WO | WO 98/56840 | | 12/1798 |

OTHER PUBLICATIONS

D.R. Rehn et al, "Marginalien Xum Thema Konservierungi", *Journal of the Society of Cosmetic Chemists*, vol. 31, No. 5, pp. 253–267 (Sep./Oct. 1980).

P.J. Collier et al, "Growth inhibitory and biocidal activity of some isothiazolone biocides", *Journal of Applied Bacteriology*, vol. 69, No. 4, pp. 569–577 (1990).

* cited by examiner

*Primary Examiner*—Alton Pryor
(74) *Attorney, Agent, or Firm*—Frishauf, Holtz, Goodman & Chick, P.C.

(57) ABSTRACT

An antimicrobial composition which comprises an isothiazolone compound, suppresses decomposition of the isothiazolone compound and reduces irritation of skin caused by the isothiazolone compound is provided. The antimicrobial composition comprises an isothiazolone compound of the following formula [1] or formula [2] and an aminocarboxylic acid of the following formula [3] or a derivative thereof:

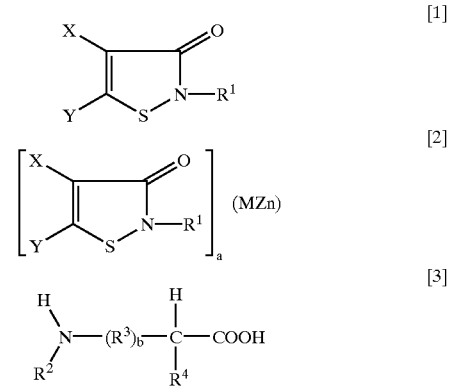

wherein $R^1$ is hydrogen, alkyl, alkenyl, alkynyl or aralkyl; X and Y are each hydrogen, halogen or form a benzene ring with the carbon atoms at the 4- and 5-positions of the isothiazolone compound; M is a cation of an alkali metal, alkaline earth metal, heavy metal or amine; Z is an anion; a is 1 or 2; n is an integer; $R^2$ is hydrogen or alkyl; $R^3$ is $C_1$–$C_5$ alkylene; $R^4$ is hydrogen or $C_1$–$C_5$ alkyl; $R^2$ and $R^4$ form a heterocyclic group; and b is 0 or 1.

21 Claims, No Drawings

ANTIBACTERIAL COMPOSITIONS

CROSS REFERENCE TO RELATED APPLICATION

This application is a United States National Phase Application under 35 USC 371 of International Application PCT/JP99/04727 (not published in English) filed Aug. 31, 1999.

TECHNICAL FIELD

The present invention relates to an antimicrobial composition. More particularly, the present invention relates to an antimicrobial composition which comprises an isothiazolone compound, suppresses decomposition of the isothiazolone compound and reduces irritation of skin caused by the isothiazolone compound.

BACKGROUND ART

Isothiazolone compounds such as 5-chloro-2-methyl-4-isothiazoline-3-one as a typical example exhibit an excellent antimicrobial property and are widely used as slime control agents, bactericides, algaecides and fungicides in various systems such as cooling water systems, paper and pulp industry, coating materials industry, adhesive materials industry, treatments of cutting oils and sewage treatments. However, isothiazolone compounds are very unstable and stability of agents containing these compounds must be improved in order to use the agents effectively. Therefore, various studies have been conducted on the improvement.

For example, in the specification of Japanese Patent Application Publication Showa 54(1979)-23968, complexes of isothiazolone compounds with metal salts such as calcium chloride and zinc chloride are proposed as a complex which have the activity for killing organisms, are useful for controlling various types of organisms, particularly microorganisms, and not easily decomposed in the presence of ordinary additives or contaminating substances or in severe conditions and show excellent heat stability. In the specification of the U.S. Pat. No. 3,870,795, it is reported that isothiazolone compounds can be stabilized by suppressing decomposition by addition of metal nitrates such as calcium nitrate and magnesium nitrate or metal nitrites such as sodium nitrite and calcium nitrite to solutions of isothiazolone compounds.

In the specifications of Japanese Patent Application Laid-Open Nos. Showa 61(1986)-56174 and Showa 61(1986)-212576, stabilized solutions of isothiazolone compounds prepared by addition of metal salts such as copper chloride, sodium chloride, magnesium chloride and copper nitrate to solutions of isothiazolone compounds such as 5-chloro-2-methyl-4-isothiazoline-3-one in propylene glycol, 1,5-pentanediol or benzyl alcohol, are proposed.

However, the above agents and solutions had drawbacks in that stability of the isothiazolone compounds markedly deteriorates when the agents and solutions are further diluted with water or organic solvents. In the specification of Japanese Patent Application Laid-Open No. Heisei 5(1993)-124917, a method for protecting isothiazolone compounds from decomposition using compounds containing sulfur such as L-cystine in combination with isothiazolone compounds is proposed. However, this method has a drawback in that L-cystine has a small solubility in water and hydrophilic organic solvents and it is difficult to mix L-cystine with isothiazolone compounds. Therefore, an antimicrobial compound which suppresses decomposition of isothiazolone compounds and shows excellent stability has been desired.

Isothiazolone compounds often irritate skin and agents containing isothiazolone compounds must be handled with sufficient care. In the specification of Japanese Patent Application Laid-Open No. Heisei 5(1993)-246807, compositions containing polycation compounds such as polylysine and isothiazolone compounds are disclosed. However, it is known that these compositions do not show the effect of suppressing decomposition of the isothiazolone compounds.

DISCLOSURE OF THE INVENTION

An object of the present invention is to provide an antimicrobial composition which comprises an isothiazolone compound, suppresses decomposition of the isothiazolone compound and reduces irritation of skin caused by the isothiazolone compound.

As the result of extensive studies to achieve the above object, it was found that specific aminocarboxylic acids and derivatives thereof exhibit the effect of stabilizing isothiazolone compounds and reducing irritation of skin caused by isothiazolone compounds. The present invention has been completed on the basis this knowledge.

The present invention provides:

(1) An antimicrobial composition comprising an isothiazolone compound represented by general formula [1] or general formula [2] and an aminocarboxylic acid represented by general formula [3] or a derivative of the aminocarboxylic acid:

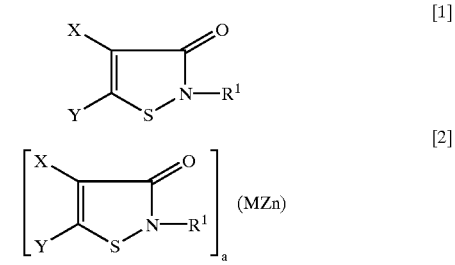

wherein $R^1$ represents hydrogen atom, an alkyl group, an alkenyl group, an alkynyl group or an aralkyl group, X and Y each represents hydrogen atom or a halogen atom or form a benzene ring in combination with carbon atoms at 4- and 5-positions of the isothiazolone compound, M represents a cation of an alkali metal, an alkaline earth metal, a heavy metal or an amine, Z represents an anion forming, in combination with the cation represented by M, a compound having a sufficient solubility to form a complex compound, a represents 1 or 2 and n represents an integer required for the anion represented by Z to satisfy a valence of the cation represented by M;

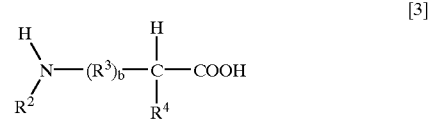

wherein $R^2$ represents hydrogen atom or an alkyl group having 1 to 5 carbon atoms unsubstituted or substituted with carboxyl group, $R^3$ represents a linear or branched alkylene group having 1 to 5 carbon atoms, $R^4$ represents hydrogen atom or an alkyl group having 1 to 5 carbon atoms unsubstituted or substituted with carboxyl group, carbamoyl group, hydroxyl group, phenyl group, hydroxyphenyl group, ureido group, methylthio group or 4-imidazolyl group, $R^2$ and $R^4$ form a heterocyclic group unsubstituted or substituted with hydroxyl group or oxo group in combination with N—$(R^3)_b$—C and b represents 0 or 1; and (2) An antimicrobial composition according to (1), wherein the derivative of the aminocarboxylic acid represented by general formula [3] is a metal salt of the aminocarboxylic acid represented by general formula [3]; a compound having a structure in which the aminocarboxylic acids represented by general formula [3] of one or more types are bonded to each other through a peptide bond or a metal salt of the compound; a compound having a structure in which the aminocarboxylic acid represented by general formula [3] is bonded to a different aminocarboxylic acid through a peptide bond or a metal salt of the compound; an N-acetyl compound of the aminocarboxylic acid represented by general formula [3] or a metal salt of the compound; or an amide of the aminocarboxylic acid represented by general formula [3].

Preferable embodiments of the present invention include:

(3) An antimicrobial composition described in any of (1) and (2), which comprises 0.1 to 10% by weight of the isothiazolone compound represented by general formula [1] or general formula [2]; and (4) An antimicrobial composition described in any of (1), (2) and (3), which comprises the aminocarboxylic acid or the derivative thereof represented by general formula [3] in an amount by mol 0.1 to 50 times the amount by mol of the isothiazolone compound represented by general formula [1] or general formula [2].

THE MOST PREFERRED EMBODIMENT TO CARRY OUT THE INVENTION

The antimicrobial composition of the present invention comprises an isothiazolone compound represented by general formula [1] or general formula [2] and an aminocarboxylic acid represented by general formula [3] or a derivative of the aminocarboxylic acid.

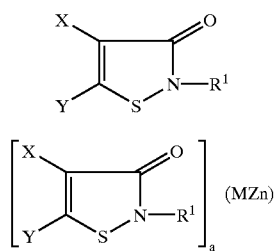

In general formula [1] and general formula [2], $R^1$ represents hydrogen atom, an alkyl group, an alkenyl group, an alkynyl group or an aralkyl group, X and Y each represents hydrogen atom or a halogen atom or form a benzene ring in combination with carbon atoms at 4- and 5-positions of the isothiazolone compound, M represents a cation of an alkali metal, an alkaline earth metal, a heavy metal or an amine, Z represents an anion forming, in combination with the cation represented by M, a compound having a sufficient solubility to form a complex compound, a represents 1 or 2 and n represents an integer required for the anion represented by Z to satisfy a valence of the cation represented by M.

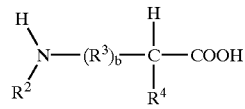

In general formula [3], $R^2$ represents hydrogen atom or an alkyl group having 1 to 5 carbon atoms unsubstituted or substituted with carboxyl group, $R^3$ represents a linear or branched alkylene group having 1 to 5 carbon atoms, $R^4$ represents hydrogen atom or an alkyl group having 1 to 5 carbon atoms unsubstituted or substituted with carboxyl group (—COOH), carbamoyl group (—CONH$_2$), hydroxyl group (—OH), phenyl group (—C$_6$H$_5$), hydroxyphenyl group (—C$_6$H$_4$OH), ureido group (—NHCONH$_2$), methylthio group (SCH$_3$) or 4-imidazolyl group:

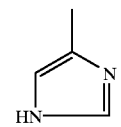

$R^2$ and $R^4$ form a heterocyclic group unsubstituted or substituted with hydroxyl group or oxo group in combination with N—$(R^3)_b$—C and b represents 0 or 1.

Examples of the isothiazolone compound represented by general formula [1] include 2-methyl-4-isothiazoline-3-one, 2-ethyl-4-isothiazoline-3-one, 2-octyl-4-isothiazoline-3-one, 5-chloro-2-methyl-4-isothiazoline-3-one, 5-chloro-2-octyl-4-isothiazoline-3-one, 4,5-dichloro-2-methyl-4-isothiazoline-3-one, 4,5-dichloro-2-octyl-4-isothiazoline-3-one and 1,2-benzoisothiazoline-3-one. Examples of the isothiazolone compound represented by general formula [2] include complex compounds of the isothiazolone compounds represented by general formula [1] with magnesium chloride, magnesium nitrate, copper chloride, copper nitrate and calcium chloride.

Examples of the aminocarboxylic acid represented by general formula [3] include glycine, alanine, β-alanine, valine, leucine, isoleucine, serine, threonine, asparagic acid, glutamic acid, asparagine, glutamine, sarcosine, citrulline, methionine, α-aminobutyric acid, β-aminobutyric acid, γ-aminobutyric acid, ε-aminocaproic acid, phenylalanine, tyrosine, histidine, proline, 4-hydroxyproline, 2-pyrrolidone-5-carboxylic acid and iminodiacetic acid.

As the compound having a structure in which the aminocarboxylic acid represented by general formula [3] is bonded through a peptide bond, compounds having a structure in which the aminocarboxylic acids represented by general formula [3] of one or more types are bonded to each other through a peptide bond are preferable. Examples of such compounds include glycylglycine, glycylglycylglycine, glycylglycyl-glycylglycine, glycylalanine, glycylasparagine, glycylleucine, glycylisoleucine, glycylphenylalanine, glycylproline, glycylsarcosine, glycylserine, glycylthreonine, glycylvaline, glycylglutamine, alanylalanine, alanylasparagine, alanylglutamine, alanylglycine, alanylphenylalanine, alanyltyrosine, β-alanylhistidine, polyasparagic acid and polyglutamic acid.

Examples of the N-acetyl compound of the aminocarboxylic acid represented by general formula [3] include N-acetylglycine, N-acetylalanine, N-acetyl-L-asparagic acid, N-acetyl-L-glutamic acid and N-acetyltyrosine.

Examples of the amide of the aminocarboxylic acid represented by general formula [3] include glycineamide.

Examples of the metal salt of the compound represented by general formula [3] and the derivatives thereof include lithium salts, sodium salts, potassium salts, calcium salts and magnesium salts.

The aminocarboxylic acids represented by general formula [3] occasionally include DL-compounds, L-compounds and D-compounds. Any of DL compounds, L-compounds and D-compounds can be used in the present invention.

In the composition of the present invention, glycine and sodium glutamate are preferably used as the aminocarboxylic acid represented by general formula [3] and the derivative thereof. Glycine and sodium glutamate have advantages in that the antimicrobial composition can be prepared rapidly since these compounds have great rates of dissolution, that the amounts by weight of these compounds are smaller when these compounds are used in a prescribed amount by mol relative to an amount by mol of the isothiazolone compound represented by general formula [1] or general formula [2] since these compounds have smaller molecular weights and that these compounds are readily available since these compounds are industrially produced in large scales.

In the composition of the present invention, the concentration of the isothiazolone compound represented by general formula [1] or general formula [2] is not particularly limited. It is preferable that the concentration is 0.1 to 10% by weight and more preferably 0.5 to 8% by weight. When the concentration of the isothiazolone compound represented by general formula [1] or general formula [2] is less than 0.1% by weight, the volume of the antimicrobial composition as a commercial product increases and there is the possibility that the product is economically disadvantageous in transportation and storage. When the concentration of the isothiazolone compound represented by general formula [1] or general formula [2] exceeds 10% by weight, there is the possibility that stability of the antimicrobial composition is adversely affected.

In the present invention, the concentration of the aminocarboxylic acid represented by general formula [3] or the derivative thereof is not particularly limited. It is preferable that the aminocarboxylic acid or the derivative thereof is used in an amount by mol 0.1 to 50 times and more preferably 1 to 10 times the amount by mol of the isothiazolone compound represented by general formula [1] or general formula [2]. When the amount of the aminocarboxylic acid represented by general formula [3] or the derivative thereof is less than the amount by mol 0.1 times the amount by mol of the isothiazolone compound, there is the possibility that stability of the antimicrobial composition is insufficient and decomposition of the isothiazolone compound tends to take place and that irritation of skin is enhanced. It is generally sufficient that the amount by mol of the aminocarboxylic acid represented by general formula [3] or the derivative thereof is 50 times the amount by mol of the isothiazolone compound or less. Stability of the antimicrobial composition or the effect of reducing irritation of skin caused by the isothiazolone compound is not improved any more even when the aminocarboxylic acid represented by general formula [3] or the derivative thereof is used in an amount by mol exceeding 50 times the amount by mol of the isothiazolone compound. When the derivative of the aminocarboxylic acid represented by general formula [3] is a polyamino acid, it is preferable that the concentration of the derivative in the antimicrobial composition is 0.1 to 20% by weight.

The solvent used in the composition of the present invention is not particularly limited as long as the isothiazolone compound represented by general formula [1] or general formula [2] and the aminocarboxylic acid represented by general formula [3] or the derivative thereof are dissolved in the solvent. Because the composition is often used in an aqueous system, water or a hydrophilic organic solvent is preferable as the solvent. Examples of the hydrophilic organic solvent include amides such as dimethylformamide; glycols such as ethylene glycol, propylene glycol, diethylene glycol and dipropylene glycol; glycol esters such as methylcellosolve, phenylcellosolve, diethylene glycol monomethyl ether and dipropylene glycol monomethyl ether; alcohols having 8 or less carbon atoms; and esters such as methyl acetate, ethyl acetate, 3-methoxybutyl acetate, 2-ethoxyethyl acetate, 2-ethoxypropyl acetate and propylene carbonate. It is preferable that pH of the antimicrobial composition of the present invention is 7 or less. It is more preferable that pH of the composition is 2 to 5 to improve stability of the isothiazolone compound.

The antimicrobial composition of the present invention may further comprise corrosion inhibitors, scale inhibitors, antimicrobial agents other than the isothiazolone compounds, defoaming agents, surfactants and algicides where necessary.

Examples of the corrosion inhibitor include tolyl triazole, benzotriazole, methylbenzotriazole, molybdic acid, tungstic acid, silicic acid, nitrous acid, 2-phosphonobutane-1,2,4-tricarboxylic acid, hydroxy-ethylidenediphosphonic acid, hexametaphosphoric acid, tripolyphosphoric acid, orthophosphoric acid, salts of these compounds, zinc chloride, zinc chloride hydrochloride, zinc sulfate, zinc ligninsulfonate and hydrazine.

Examples of the scale inhibitor include polyacrylic acid, copolymers of acrylic acid and 2-hydroxyethyl methacrylate, copolymers of acrylic acid, 2-hydroxyethyl methacrylate and methyl acrylate, copolymers of acrylic acid and allyl glycidyl ether or a derivative thereof, copolymers of acrylic acid and 2-hydroxy-3-allyloxy-1-propanesulfonic acid, copolymers of acrylic acid and isoprenesulfonic acid, copolymers of acrylic acid and vinylsulfonic acid, copolymers of acrylic acid and allylsulfonic acid, polymaleic acid, copolymers of maleic acid or maleic anhydride and isobutylene, copolymers of maleic acid or maleic anhydride and styrenesulfonic acid, copolymers of maleic acid or maleic anhydride and acrylic acid, copolymers of maleic acid or maleic anhydride and 2-acrylamido-2-methylpropanesulfonic acid, copolymers of maleic acid or maleic anhydride and pentenoic acid, copolymers of maleic acid or maleic anhydride and a fluorescent substance such as 5-allylbenzosuberenol substituted with allyl group, polyacrylamide, polyitaconic acid and salts of these compounds.

Examples of the antimicrobial agent other than the isothiazolone compounds include halogenated aliphatic nitro compounds such as 2-bromo-2-nitro-1,3-propanediol and 2,2-dibromo-2-nitroethanol; esters of these compounds; dibromonitrilopropionamide; alkylene bisthiocyanates such as methylenebisthiocyanate; 1,4-bisbromoacetoxy-2-butene; hexabromo-dimethylsulfone; isophthalonitrile compounds such as 5-chloro-2,4,6-trifluoroisophthalonitrile and tetrachloroisophthalonitrile; dimethyl dithiocarbamate; 4,5-dichloro-1,2-dithiol-3-one; 3,3,4,4-tetrachloroteterahydrothiophene-1,1-dioxide; triiodoallyl alcohol; bromonitrostyrene; aldehyde compounds such as glutaraldehyde, phthalaldehyde, isophthalaldehyde and terephthalaldehyde; dichloro-glyoxime; benzaldoxime compounds such as α-chlorobenzaldoxime acetate and α-chlorobenzaldoxime; and 5,5-dimethylhidantoin.

Examples of the defoaming agent include silicone and non-silicone defoaming agents. Examples of the surfactant include anionic, cationic, nonionic and amphoteric surfactants. Examples of the algicide include triazine compounds such as ametryne.

The embodiments of the composition of the present invention include antimicrobial compositions containing 0.1 to 10% by weight of the isothiazolone compound represented by general formula [1] or general formula [2], 0.1 to 20% by weight of the aminocarboxylic acid represented by general formula [3] or the derivative thereof, 0 to 50% by weight of corrosion inhibitors, 0 to 50% by weight of scale inhibitors, 0 to 30% by weight of other antimicrobial agents, 0 to 10% by weight of defoaming agents, 0 to 10% by weight of surfactants, 0 to 10% by weight of algicides and 30 to 99% by weight of water or a hydrophilic organic solvent.

The antimicrobial composition of the present invention can be used in a concentration suitably selected in accordance with the subject and the object of the application. For example, when the composition is used for prevention of slime in a paper and pulp manufacturing system or in a cooling water system, it is preferable that the concentration of the isothiazolone compound is 0.1 to 25 g/m$^3$. When the composition is used for prevention of putrefaction of an emulsion of a synthetic resin, a starch paste, a starch slurry, a coating material or an oil for metal working, it is preferable that the concentration of the isothiazolone compound is 1 to 5,000 g/m$^3$.

The antimicrobial composition of the present invention contains the isothiazolone compound and the aminocarboxylic acid or the derivative thereof, shows excellent stability under heating and for a long time, does not cause decomposition of the isothiazolone compound for a long time, exhibits the excellent antimicrobial effect derived from the isothiazolone compound and can be easily handled due to decreased irritation of skin caused by the isothiazolone compound.

EXAMPLES

The present invention will be described more specifically in the following with reference to examples. However, the present invention is not limited to the examples.

In the examples and the comparative examples, irritation of skin by an antimicrobial composition was evaluated in accordance with the following method.

The screening test of a prepared antimicrobial composition with respect to the irritation of skin was conducted using three white rabbits (New Zealand white strain) for each composition. A portion of a normal skin of a rabbit was used for the test. An antimicrobial composition without dilution in an amount of 0.5 ml was added to a patch of gauze and applied to the portion for the test. After the patch was kept at the portion for 4 hours, the patch was removed and the portion was washed. Irritation of the skin was visually observed after 1, 24, 48 and 72 hours and recorded in accordance with the criteria described below. The numbers with respect to the erythema and edema were added and the obtained sums were averaged to obtain a primary index for skin irritation (PII) which was in the range of 0 to 8.

Erythema and Eschar formation

0: no erythema

1: very slight erythema (barely perceptible)

2: well-defined erythema

3: moderate to severe erythema

4; severe erythema (beet redness) to slight eschar formation (injuries in depth)

Edema formation

0: no edema

1: very slight edema (barely perceptible)

2: slight edema (edges of area well-defined by definite raising)

3: moderate edema (raised approximately 1 mm)

4: severe edema (raised more than 1 mm and extending beyond the area of exposure)

Example 1

An ethylene glycol solution (ZONEN-F; manufactured by ICHIKAWA GOSEI KAGAKU Co., Ltd.) containing 11% by weight of 5-chloro-2-methyl-4-isothiazoline-3-one and 1% by weight of 2-methyl-4-isothiazoline-3-one in an amount of 5.0 parts by weight, 0.62 parts by weight of glycine and 94.38 parts by weight of water were mixed to form a homogeneous solution and an antimicrobial composition was prepared.

The prepared antimicrobial composition contained glycine in an amount by mol twice the total amount by mol of 5-chloro-2-methyl-4-isothiazoline-3-one and 2-methyl-4-isothiazoline-3-one.

Additionally, 25 types of antimicrobial compositions were prepared using, in place of glycine, alanine, β-alanine, DL-serine, DL-threonine, DL-asparagine, L-glutamine, sarcosine, DL-p-aminobutyric acid, γ-aminobutyric acid, DL-methionine, iminodiacetic acid, glycylglycine, glycylglycylglycine, glycylglycylglycylglycine, glycyl-L-glutamine, L-alanyl-L-glutamine, β-alanyl-L-histidine, pyrrolidonecarboxylic acid, N-acetylglycine, N-acetyl-L-tyrosine, sodium L-asparagate, sodium L-glutamate, citrulline, phenylalanine or glycineamide as the aminocarboxylic acid represented by general formula [3] or the derivative thereof. An ethylene glycol solution (ZONEN-F; manufactured by ICHIKAWA GOSEI KAGAKU Co., Ltd.) containing 11% by weight of 5-chloro-2-methyl-4-isothiazoline-3-one and 1% by weight of 2-methyl-4-isothiazoline-3-one in an amount of 5.0 parts by weight and the aminocarboxylic acid represented by general formula [3] or the derivative thereof in an amount by mol twice the total amount by mol of 5-chloro-2-methyl-4-isothiazoline-3-one and 2-methyl-4-isothiazoline-3-one and water in an amount such that the total amount of the composition was 100.0 parts by weight were mixed to form a homogeneous solution.

The obtained 26 types of antimicrobial compositions were left standing at the room temperature for one month. The compositions remained as transparent liquids and no precipitates were found.

Comparative Example 1

An ethylene glycol solution (ZONEN-F; manufactured by ICHIKAWA GOSEI KAGAKU Co., Ltd.) containing 11% by weight of 5-chloro-2-methyl-4-isothiazoline-3-one and 1% by weight of 2-methyl-4 -isothiazoline-3-one in an amount of 5.0 parts by weight and 95.0 parts by weight of water were mixed to form a homogeneous solution and an antimicrobial composition was prepared.

The prepared antimicrobial composition was left standing at the room temperature for one month. Yellow orange precipitates were formed in the composition.

The results of Example 1 and Comparative Example 1 are shown in Table 1.

TABLE 1

| | Aminocarboxylic acid or derivative thereof | Appearance after one month |
|---|---|---|
| Example 1 | | |
| No. 1 | glycine | transparent liquid, no precipitates |
| No. 2 | alanine | transparent liquid, no precipitates |
| No. 3 | β-alanine | transparent liquid, no precipitates |
| No. 4 | DL-serine | transparent liquid, no precipitates |
| No. 5 | DL-threonine | transparent liquid, no precipitates |
| No. 6 | DL-asparagine | transparent liquid, no precipitates |
| No. 7 | L-glutamine | transparent liquid, no precipitates |
| No. 8 | sarcosine | transparent liquid, no precipitates |
| No. 9 | DL-β-aminobutyric acid | transparent liquid, no precipitates |
| No. 10 | γ-aminobutyric acid | transparent liquid, no precipitates |
| No. 11 | DL-methionine | transparent liquid, no precipitates |
| No. 12 | iminodiacetic acid | transparent liquid, no precipitates |
| No. 13 | glycylglycine | transparent liquid, no precipitates |
| No. 14 | glycylglycylglycine | transparent liquid, no precipitates |
| No. 15 | glycylglycylglycylglycine | transparent liquid, no precipitates |
| No. 16 | glycyl-L-glutamine | transparent liquid, no precipitates |
| No. 17 | L-alanyl-L-glutamine | transparent liquid, no precipitates |
| No. 18 | β-alanyl-L-histidine | transparent liquid, no precipitates |
| No. 19 | pyrrolidonecarboxylic acid | transparent liquid, no precipitates |
| No. 20 | N-acetylglycine | transparent liquid, no precipitates |
| No. 21 | N-acetyl-L-tyrosine | transparent liquid, no precipitates |
| No. 22 | sodium L-asparagate | transparent liquid, no precipitates |
| No. 23 | sodium L-glutamate | transparent liquid, no precipitates |
| No. 24 | citrulline | transparent liquid, no precipitates |
| No. 25 | phenylalanine | transparent liquid, no precipitates |
| No. 26 | glycineamide | transparent liquid, no precipitates |
| Comparative Example 1 | none | yellow orange precipitates |

As shown by the results in Table 1, precipitates were formed in the antimicrobial composition of Comparative Example 1 which contained 5-chloro-2-methyl-4-isothiazoline-3-one and 2-methyl-4-isothiazoline-3-one but did not contain the aminocarboxylic acid represented by general formula [3] or the derivative thereof after the composition was left standing at the room temperature for one month. In contrast, the antimicrobial compositions of Example 1 which contained the aminocarboxylic acid represented by general formula [3] or the derivative thereof showed no change in the appearance after the compositions were left standing at the room temperature for one month and exhibited excellent stability for a long time.

Example 2

From the 26 types of antimicrobial compositions prepared in Example 1, 23 types of compositions were selected and left standing in a constant temperature oven kept at 60° C. for 48 hours. Then, the content of 5-chloro-2-methyl-4-isothiazoline-3-one was measured in accordance with the high performance liquid chromatography and the residue was calculated. The residue of 5-chloro-2-methyl-4-isothiazoline-3-one in the antimicrobial composition containing glycine was 76%. The residues of other antimicrobial compositions are shown in Table 2.

Comparative Example 2

The antimicrobial composition prepared in Comparative Example 1 was left standing in a constant temperature oven kept at 60° C. for 48 hours. Then, the content of 5-chloro-2-methyl-4-isothiazoline-3-one was measured in accordance with the high performance liquid chromatography. No peaks of 5-chloro-2-methyl-4-isothiazoline-3-one were found in the chromatogram. This shows that 5-chloro-2-methyl-4-isothiazoline-3-one was completely decomposed.

Comparative Example 3

An ethylene glycol solution (ZONEN-F; manufactured by ICHIKAWA GOSEI KAGAKU Co., Ltd.) containing 11% by weight of 5-chloro-2-methyl-4-isothiazoline-3-one and 1% by weight of 2-methyl-4-isothiazoline-3-one in an amount of 5.0 parts by weight, 2.0 parts by weight of polylysine and 93.0 parts by weight of water were mixed to form a homogeneous solution and an antimicrobial composition was prepared.

The antimicrobial composition prepared above was left standing in a constant temperature oven kept at 60° C. for 48 hours. Then, the content of 5-chloro-2-methyl-4-isothiazoline-3-one was measured in accordance with the high performance liquid chromatography. No peaks of 5-chloro-2-methyl-4-isothiazoline-3-one were found in the chromatogram. This shows that 5-chloro-2-methyl-4-isothiazoline-3-one was completely decomposed.

The results of Example 2 and Comparative Examples 2 and 3 are shown in Table 2.

TABLE 2

| | Aminocarboxylic acid or derivative thereof | residual 5-chloro-2-methyl-4-isothiazoline-3-one (%) |
|---|---|---|
| Example 1 | | |
| No. 1 | glycine | 76 |
| No. 2 | alanine | 60 |
| No. 3 | β-alanine | 58 |
| No. 4 | DL-serine | 71 |
| No. 5 | DL-threonine | 76 |
| No. 6 | DL-asparagine | 67 |
| No. 7 | L-glutamine | 78 |
| No. 8 | sarcosine | 60 |
| No. 9 | DL-β-aminobutyric acid | 73 |
| No. 10 | γ-aminobutyric acid | 61 |
| No. 11 | DL-methionine | 45 |
| No. 12 | iminodiacetic acid | 99 |
| No. 13 | glycylglycine | 100 |
| No. 14 | glycylglycylglycine | 100 |
| No. 15 | glycylglycylglycylglycine | 100 |
| No. 16 | glycyl-L-glutamine | 100 |
| No. 17 | L-alanyl-L-glutamine | 100 |
| No. 18 | β-alanyl-L-histidine | 88 |
| No. 19 | pyrrolidonecarboxylic acid | 52 |
| No. 20 | N-acetylglycine | 35 |
| No. 21 | N-acetyl-L-tyrosine | 62 |
| No. 22 | sodium L-asparagate | 68 |
| No. 23 | sodium L-glutamate | 74 |
| Comparative Example 2 | none | 0 |
| Comparative Example 3 | polylysine | 0 |

As shown by the results in Table 2, 5-chloro-2-methyl-4-isothiazoline-3-one was completely decomposed in the antimicrobial composition of Comparative Example 2 which contained 5-chloro-2-methyl-4-isothiazoline-3-one and 2-methyl-4-isothiazoline-3-one but did not contain the aminocarboxylic acid represented by general formula [3] or the derivative thereof after the composition was left standing at 60° C. for 48 hours. In contrast, the antimicrobial compositions of Example 2 which contained the aminocarboxylic acid represented by general formula [3] or the derivative thereof showed a great residue of 5-chloro-2-methyl-4-isothiazoline-3-one after the compositions were left standing at 60° C. for 48 hours and exhibited excellent heat stability. In particular, 5-chloro-2-methyl-4-isothiazoline-3-one was not decomposed at all and the residue remained at 100% in the antimicrobial compositions containing glycylglycine, glycylglycylglycine, glycylglycylglycylglycine, glycyl-L-glutamine or L-alanyl-L-glutamine, i.e., the compound having a structure in which the aminocarboxylic acids represented by general formula [3] were bonded to each other through a peptide bond. The antimicrobial composition of Comparative Example 3 containing a compound having a structure which is close to the aminocarboxylic acid represented by general formula [3] but in which the group represented by $R^4$ is an alkyl group substituted with amino group, i.e., polylysine, showed inferior heat stability and 5-chloro-2-methyl-4-isothiazoline-3-one was completely decomposed after the composition was left standing at 60° C. for 48 hours.

Example 3

An aqueous solution (KATHON-WT; manufactured by ROHM & HAAS Company) containing 11% by weight of 5-chloro-2-methyl-4-isothiazoline-3-one, 3% by weight of 2-methyl-4-isothiazoline-3-one, magnesium chloride and magnesium nitrate was used in place of the ethylene glycol solution (ZONEN-F; manufactured by ICHIKAWA GOSEI KAGAKU Co., Ltd.) containing 11% by weight of 5-chloro-2-methyl-4-isothiazoline-3-one and 1% by weight of 2-methyl-4-isothiazoline-3-one. Glycylglycine, glycylglycylglycine, glycylglycylglycylglycine, glycyl-L-glutamine or L-alanyl-L-glutamine was used as the aminocarboxylic acid represented by general formula [3] or the derivative thereof Five types of antimicrobial compositions were prepared in accordance with the same procedures as those conducted in Example 2. The prepared compositions were left standing in a constant temperature oven kept at 60° C. for 48 hours. Then, the content of 5-chloro-2-methyl-4-isothiazoline-3-one was measured in accordance with the high performance liquid chromatography.

The residue of 5-chloro-2-methyl-4-isothiazoline-3-one was 100% in all compositions.

Comparative Example 4

An aqueous solution (KATHON-WT; manufactured by ROHM & HAAS Company) containing 11% by weight of 5-chloro-2-methyl-4-isothiazoline-3-one, 3% by weight of 2-methyl-4-isothiazoline-3-one, magnesium chloride and magnesium nitrate in an amount of 5 parts by weight and 95.0 parts by weight of water were mixed to form a homogeneous solution and an antimicrobial composition was prepared.

The prepared compositions were left standing in a constant temperature oven kept at 60° C. for 48 hours. Then, the content of 5-chloro-2-methyl-4-isothiazoline-3-one was measured in accordance with the high performance liquid chromatography. The residue of 5-chloro-2-methyl-4-isothiazoline-3-one was 51%.

The results of Example 3 and Comparative Example 4 are shown in Table 3.

TABLE 3

| | Aminocarboxylic acid or derivative thereof | residual 5-chloro-2-methyl-4-isothiazoline-3-one (%) |
| --- | --- | --- |
| Example 3 | | |
| No. 13 | glycylglycine | 100 |
| No. 14 | glycylglycylglycine | 100 |
| No. 15 | glycylglycylglycylglycine | 100 |
| No. 16 | glycyl-L-glutamine | 100 |
| No. 17 | L-alanyl-L-glutamine | 100 |
| Comparative Example 4 | none | 51 |

As shown by the results in Table 3, 5-chloro-2-methyl-4-isothiazoline-3-one in the antimicrobial compositions of Example 3 containing glycylglycine, glycylglycylglycine, glycylglycylglycylglycine, glycyl-L-glutamine or L-alanyl-L-glutamine, i.e., the compound in which the aminocarboxylic acids represented by general formula [3] were bonded to each other through a peptide bond, was not decomposed at all and the residue remained at 100% after the compositions were left standing at 60° C. for 48 hours. In contrast, the antimicrobial composition of Comparative Example 4 which did not contain the aminocarboxylic acid represented by general formula [3] or the derivative thereof showed inferior heat stability and about a half of the amount of 5-chloro-2-methyl-4-isothiazoline-3-one was decomposed after the composition was left standing at 60° C. for 48 hours.

Example 4

An ethylene glycol solution (ZONEN-F; manufactured by ICHIKAWA GOSEI KAGAKU Co., Ltd.) containing 11% by weight of 5-chloro-2-methyl-4-isothiazoline-3-one and 1% by weight of 2-methyl-4-isothiazoline-3-one in an amount of 5.0 parts by weight, 1.09 parts by weight of glycylglycine and 93.91 parts by weight of water were mixed to form a homogeneous solution and an antimicrobial composition was prepared. The prepared antimicrobial composition contained glycylglycine in an amount by mol twice the total amount by mol of 5-chloro-2-methyl-4-isothiazoline-3-one and 2-methyl-4-isothiazoline-3-one. Using *Bacilus subtillus*, the prepared composition was examined with respect to the effect of suppressing growth of the bacteria.

Into a liquid medium containing 1 g/liter of peptone and 1 g/liter of yeast extract and having pH of 7, *Bacilus subtillus* was inoculated in an amount of $10^6$ bacteria/ml. To the inoculated medium, the above antimicrobial composition was added in an amount such that the concentration was 20 mg/liter, 60 mg/liter or 100 mg/liter. The obtained medium was cultured at 30° C. for 24 hours while being shaken. The effect of suppressing growth of the bacteria was found when the concentration was 60 mg/liter and 100 mg/liter although the effect was not found when the concentration was 20 mg/liter.

After the above antimicrobial composition was left standing at the room temperature for one month, the composition was examined with respect to the effect of suppressing growth of the bacteria in accordance with the same procedures as those conducted above. The effect of suppressing growth of the bacteria was found when the concentration was 60 mg/liter and 100 mg/liter although the effect was not found when the concentration was 20 mg/liter.

Comparative Example 5

An ethylene glycol solution (ZONEN-F; manufactured by ICHIKAWA GOSEI KAGAKU Co., Ltd.) containing 11% by weight of 5-chloro-2-methyl-4-isothiazoline-3-one and 1% by weight of 2-methyl-4-isothiazoline-3-one in an amount of 5.0 parts by weight and 95 parts by weight of water were mixed to form a homogeneous solution and an antimicrobial composition was prepared. Using *Bacilus subtillus*, the prepared composition was examined with respect to the effect of suppressing growth in accordance with the same procedures as those conducted in Example 4. The effect of suppressing growth of the bacteria was found when the concentration was 60 mg/liter and 100 mg/liter although the effect was not found when the concentration was 20 mg/liter.

After the above antimicrobial composition was left standing at the room temperature for one month, the composition was examined with respect to the effect of suppressing growth of the bacteria in accordance with the same procedures as those above. The effect of suppresing growth of the bacteria was not found in any of the cases where the concentration was 20 mg/liter, 60 mg/liter, and 100 mg/liter.

The results of Example 4 and Comparative Example 5 are shown in

TABLE 4

| time of test | concentration of antimicrobial composition (mg/liter) | effect of suppressing growth of the bacteria |
|---|---|---|
| Example 4 | | |
| immediately after preparation | 20 | not exhibited |
| | 60 | exhibited |
| | 100 | exhibited |
| after 1 month at room temp. | 20 | not exhibited |
| | 60 | exhibited |
| | 100 | exhibited |
| Comparative Example 5 | | |
| immediately after preparation | 20 | not exhibited |
| | 60 | exhibited |
| | 100 | exhibited |
| after 1 month at room temp. | 20 | not exhibited |
| | 60 | not exhibited |
| | 100 | not exhibited |

As shown by the results in Table 4, the antimicrobial composition prepared in Comparative Example 5 lost effect of suppressing growth of *Bacillus subtillus* after the composition was left standing at the room temperature for one month. In contrast, the antimicrobial composition prepared in Example 4 which contained glycylglycine held the effect of suppressing growth of the bacteria after the composition was left standing at the room temperature for one month. Thus, it is shown that the antimicrobial composition of the present invention exhibits excellent stability for a long time.

Example 5

Glycine, sodium L-glutamate, iminodiacetic acid or glycylglycine was used as the aminocarboxylic acid represented by general formula [3] or the derivative thereof. An ethylene glycol solution (ZONEN-F; manufactured by ICHIKAWA GOSEI KAGAKU Co., Ltd.) containing 11% by weight of 5-chloro-2-methyl-4-isothiazoline-3-one and 1% by weight of 2-methyl-4-isothiazoline-3-one in an amount of 5.0 parts by weight, the aminocarboxylic acid represented by general formula [3] or the derivative thereof in an amount by mol twice the total amount by mol of 5-chloro-2-methyl-4-isothiazoline-3-one and 2-methyl-4-isothiazoline-3-one and water in an amount such that the total amount of the composition was 100.0 parts by weight were mixed to form a homogeneous solution and 4 types of antimicrobial compositions were prepared.

The above test of irritation of skin was conducted using the prepared antimicrobial compositions.

Comparative Example 6

An ethylene glycol solution (ZONEN-F; manufactured by ICHIKAWA GOSEI KAGAKU Co., Ltd.) containing 11% by weight of 5-chloro-2-methyl-4-isothiazoline-3-one and 1% by weight of 2-methyl-4-isothiazoline-3-one in an amount of 5.0 parts by weight and 95.0 parts by weight of water were mixed to form a homogeneous solution and an antimicrobial composition was prepared.

The above test of irritation of skin was conducted using the prepared antimicrobial composition.

The results of Example 5 and Comparative Example 6 are shown in Table 5.

TABLE 5

| amino-carboxylic acid | number obtained by evaluation | | | | | primary index for skin irritation |
|---|---|---|---|---|---|---|
| | irritation | time (hour) | | | | |
| | | 1 | 24 | 48 | 72 | |
| Example 5 | | | | | | |
| glycine | erythema | 2.33 | 2.33 | 2.67 | 3.33 | 5.67 |
| | edema | 4.00 | 3.00 | 3.00 | 2.00 | |
| | total | 6.33 | 5.33 | 5.67 | 5.33 | |
| sodium L-glutamate | erythema | 2.33 | 2.33 | 2.67 | 3.33 | 5.67 |
| | edema | 4.00 | 3.00 | 3.00 | 2.00 | |
| | total | 6.33 | 5.33 | 5.67 | 5.33 | |
| iminodiacetic acid | erythema | 2.33 | 3.00 | 2.67 | 3.33 | 5.42 |
| | edema | 4.00 | 2.33 | 2.00 | 2.00 | |
| | total | 6.33 | 5.33 | 4.67 | 5.33 | |
| glycylglycine | erythema | 2.00 | 2.67 | 2.67 | 2.67 | 5.25 |
| | edema | 4.00 | 2.67 | 2.33 | 2.00 | |
| | total | 6.00 | 5.34 | 5.00 | 4.67 | |
| Comparative Example 6 | | | | | | |
| none | erythema | 3.33 | 3.00 | 3.33 | 3.33 | 7.25 |
| | edema | 4.00 | 4.00 | 4.00 | 4.00 | |
| | total | 7.33 | 7.00 | 7.33 | 7.33 | |

The results of Example 5 and Comparative Example 6 in Table 5 were obtained under the same condition except that the aminocarboxylic acid or the derivative thereof was present in Example 5 and absent in Comparative Example 6. When these results are compared, it is shown that the antimicrobial compositions prepared in Example 5 which contained glycine, sodium L-glutamate, iminodiacetic acid or glycylglycine showed smaller primary indices of skin irritation than the antimicrobial composition prepared in Comparative Example 6 which did not contain the aminocarboxylic acid or the derivative thereof. Thus, it is shown that irritation of skin caused by the antimicrobial composition containing the isothiazolone compound was reduced when the composition contained the aminocarboxylic acid or the derivative thereof

INDUSTRIAL APPLICABILITY

The antimicrobial composition of the present invention comprises the isothiazolone compound and the aminocarboxylic acid or the derivative thereof, shows excellent stability for a long time and excellent heat stability, suppresses decomposition of the isothiazolone compound even after storage for a long time, exhibits the excellent antimicrobial effect of the isothiazolone compound, reduces irritation of skin caused by the isothiazolone compound and can be handled easily.

What is claimed is:

1. An antimicrobial composition consisting essentially of (i) 0.5 to 8% by weight of an isothiazolone compound selected from the group consisting of a compound of the following formula [1] and a compound of the following formula [2], and (ii) an aminocarboxylic acid of the following formula [3], the aminocarboxylic acid being in an amount of moles of 0.1 to 50 times the amount of moles of the isothiazolone compound, the isothiazolone compound and the aminocarboxylic acid both being dissolved in a solvent of water and optionally a hydrophilic solvent;

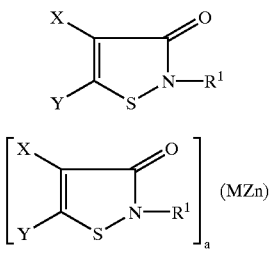

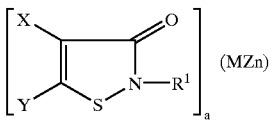

wherein $R^1$ represents a hydrogen atom, an alkyl group, an alkenyl group, an alkynyl group or an aralkyl group, X and Y each represents a hydrogen atom or a halogen atom or form a benzene ring in combination with carbon atoms at the 4- and 5-positions of the isothiazolone compound, M represents a cation of an alkali metal, an alkaline earth metal, a heavy metal or an amine, Z represents an anion forming, in combination with the cation represented by M, a compound having a sufficient solubility to form a complex compound, a represents 1 or 2 and n represents an integer required for the anion represented by Z to satisfy a valence of the cation represented by M;

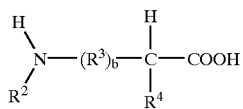

wherein $R^2$ represents a hydrogen atom or an alkyl group having 1 to 5 carbon atoms unsubstituted or substituted with a carboxyl group, $R^3$ represents a linear or branched alkylene group having 1 to 5 carbon atoms, $R^4$ represents a hydrogen atom or an alkyl group having 1 to 5 carbon atoms unsubstituted or substituted with a carboxyl group, a carbamoyl group, a hydroxyl group, a phenyl group, a hydroxyphenyl group, an ureido group, a methylthio group or a 4-imidazolyl group, $R^2$ and $R^4$ form a heterocyclic group unsubstituted or substituted with a hydroxyl group or an oxo group in combination with N—$(R^3)_b$—C and b represents 0 or 1.

2. An antimicrobial composition consisting essentially of (i) 0.5 to 8% by weight of an isothiazolone compound selected from the group consisting of the compound of the formula [1] according to claim 1 and the compound of the formula [2] according to claim 1 and (ii) an aminocarboxylic acid compound selected from the group consisting of (a) a metal salt of the aminocarboxylic acid of the formula [3] according to claim 1; (b) a compound having a structure in which aminocarboxylic acids of said formula [3] are bonded to each other through a peptide bond or a metal salt of the compound; (c) a compound having a structure in which the aminocarboxylic acid of said formula [3] is bonded to a different aminocaboxylic acid through a peptide bond or a metal salt of the compound; (d) an N-acetyl compound of the aminocarboxylic acid of said formula [3] or a metal salt of the compound; and (e) an amide of the aminocarboxylic acid of said formula [3], the aminocarboxylic acid compound being in an amount of moles of 0.1 to 50 times the amount of moles of the isothiazolone compound, the isothiazolone compound and the aminocarboxylic acid compound both being dissolved in a solvent of water and optionally a hydrophilic solvent.

3. An antimicrobial composition according to claim 1, wherein the aminocarboxylic acid of the formula [3] is in an amount of moles of 1 to 10 times the amount by moles of the isothiazolone compound.

4. An antimicrobial composition according to claim 1, wherein the isothiazolone compound of the formula [1] or the isothiazolone compound of the formula [2] and the aminocarboxylic acid of the formula [3] are dissolved in a mixed solvent of water and a hydrophilic solvent.

5. An antimicrobial composition according to claim 1, wherein the isothiazolone compound is of the formula [1] and is 5-chloro-2-methyl-4-isothiazoline-3-one.

6. An antimicrobial composition according to claim 1, wherein the isothiazolone compound is of the formula [2] and is a complex compound of 5-chloro-2-methyl-4-isothiazoline-3-one with magnesium chloride or magnesium nitrate.

7. An antimicrobial composition according to claim 1, wherein the aminocarboxylic acid of the formula [3] is glycine.

8. An antimicrobial composition according to claim 1, wherein the aminocarboxylic acid of the formula [3] is iminodiacetic acid.

9. An antimicrobial composition according to claim 2, wherein the aminocarboxylic acid compound is glycylglycine.

10. An antimicrobial composition according to claim 2, wherein the aminocarboxylic acid compound is glycylglycylglycine.

11. An antimicrobial composition according to claim 2, wherein the aminocarboxylic acid compound is glycyl-L-glutamine.

12. An antimicrobial composition according to claim 2, wherein the aminocarboxylic acid compound is L-alanyl-L-glutamine.

13. An antimicrobial composition according to claim 2, wherein the aminocarboxylic acid compound is β-alanyl-L-histidine.

14. An antimicrobial composition according to claim 2, wherein the aminocarboxylic acid compound is sodium L-glutamate.

15. A method for combatting microbes comprising applying to microbes or to a locus thereof an antimicrobial amount of the antimicrobial composition according to claim 1.

16. A method for combatting slime in a system selected from the group consisting of (a) a paper and pulp manufacturing system and (b) a cooling water system comprising applying to said system an anti-slime effective amount of the antimicrobial composition according to claim 1.

17. An antimicrobial composition according to claim 1, wherein the isothiazolone compound is selected from the group consisting of 2-methyl-4-isothiazoline-3-one, 2-ethyl-4-isothiazoline-3-one, 2-octyl-4-isothiazoline-3-one, 5-chloro-2-methyl-4-isothiazoline-3-one, 5-chloro-2-octyl-4-isothiazoline-3-one, 4,5-dichloro-2-methyl-4-isothiazoline-3-one, 4,5-dichloro-2-octyl-4-isothiazoline-3-one and 1,2-benzoisothiazoline-3-one; and the aminocarboxylic acid is selected from the group consisting of glycine, alanine, β-alanine, valine, leucine, isoleucine, serine, threonine, asparagic acid, glutamic acid, asparagine, glutamine, sarcosine, citrulline, methionine, α-aminobutyric acid, β-aminobutyric acid, γ-aminobutyric acid, ε-aminocaproic acid, phenylalanine, tyrosine, histidine, proline, 4-hydroxyproline, 2-pyrrolidine-5-carboxylic acid and iminodiacetic acid.

18. An antimicrobial composition according to claim 2, wherein the isothiazlone compound is selected from the group consisting of 2-methyl-4-isothiazoline-3-one, 2-ethyl-4-isothiazoline-3-one, 2-octyl-4-isothiazoline-3-one, 5-chloro-2-methyl-4-isothiazoline-3-one, 5-chloro-2-octyl-4-isothiazoline-3-one, 4,5-dichloro-2-methyl-4-isothiazoline-3-one, 4,5-dichloro-2-octyl-4-isothiazoline-3-one and 1,2-benzoisothiazoline-3-one; and the aminocarboxylic acid is selected from the group consisting of glycylglycine, glycylglycylglycine, glycylglycylglycylglycine, glycylalanine, glycylasparagine, glycylleucine, glycylisoleucine, glycylphenylalanine, glycylproline, glycylsarcosine, glycylserine, glycylthreonine, glycylvaline, glycylglutamine, alanylalanine, alanylasparagine, alanylglutamine, alanylglycine, alanylphenylalanine, alanylthyrosine, β-alanylhistidine, polyasparagic acid, polyglutamic acid, N-acetylglycine, N-acetylalanine, N-acetyl-L-asparagic acid, N-acetyl-L-glutamic acid, N-acetyltyrosine and glycineamide.

19. A method for suppressing the decomposition of a solution consisting essentially of an isothiazolone compound in an aqueous solution or in a mixed solution of water and a hydrophilic solvent and for reducing skin irritation caused by the solution of the isothiazolone compound comprising adding to the solution an effective amount of a compound consisting essentially of an aminocarboxylic acid of the following formula [3]:

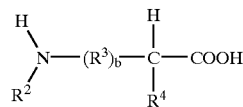

wherein $R^2$ represents a hydrogen atom or an alkyl group having 1 to 5 carbon atoms unsubstituted or substituted with a carboxyl group, $R^3$ represents a linear or branched alkylene group having 1 to 5 carbon atoms, $R^4$ represents a hydrogen atom or an alkyl group having 1 to 5 carbon atoms unsubstituted or substituted with a carboxyl group, a carbamoyl group, a hydroxyl group, a phenyl group, a hydrophenyl group, an ureido group, a methylthio group or a 4-imidazolyl group, $R^2$ and $R^4$ form a heterocyclic group unsubstituted or substituted with a hydroxyl group or an oxo group in combination with N—$(R^3)_b$—C and b represents 0 or 1.

20. An antimicrobial composition consisting essentially of
(i) 0.5 to at by weight of an isothiazolone compound selected from the group consisting of a compound of the following formula [1] and a compound of the following formula [2], (ii) an aminocarboxylic acid of the following formula [3], and (iii) at least one substance selected from the group consisting of a corrosion inhibitor, a scale inhibitor, an antimicrobial agent other than an isothiazolone compound, a defoaming agent, a surfactant and an algicide, the aminocarboxylic acid being in an amount of moles of 0.1 to 50 times the amount of moles of the isothiazolone compound, the isothiazolone compound and the aminocarboxylic acid both being dissolved in a solvent of water and optionally a hydrophilic solvent:

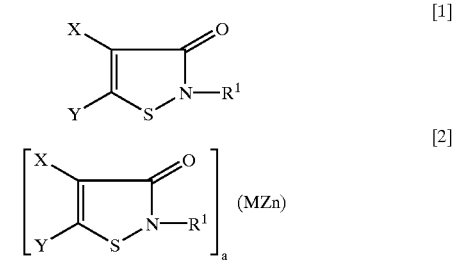

wherein $R^1$ represents a hydrogen atom, an alkyl group, an alkenyl group, an alkynyl group or an aralkyl group, X and Y each represents a hydrogen atom or a halogen atom or form a benzene ring in combination with carbon atoms at the 4- and 5-positions of the isothiazolone compound, M represents a cation of an alkali metal, an alkaline earth metal, a heavy metal or an amine, Z represents an anion forming, in combination with the cation represented by M, a compound having a sufficient solubility to form a complex compound, a represents 1 or 2 and n represents an integer required for the anion represented by Z to satisfy a valence of the cation represented by M;

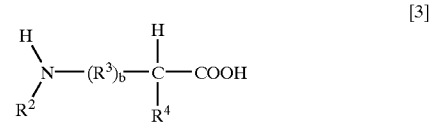

wherein $R^2$ represents a hydrogen atom or an alkyl group having 1 to 5 carbon atoms unsubstituted or substituted with a carboxyl group, $R^3$ represents a linear or branched alkylene group having 1 to 5 carbon atoms, $R^4$ represents a hydrogen atom or an alkyl group having 1 to 5 carbon atoms unsubstituted or substituted with a carboxyl group, a carbamoyl group, a hydroxyl group, a phenyl group, a hydrophenyl group, an ureido group, a methylthio group or a 4-imidazolyl group, $R^2$ and $R^4$ form a heterocyclic group unsubstituted or substituted with a hydroxyl group or an oxo group in combination with N—$(R^3)_b$—C and b represents 0 or 1.

21. An antimicrobial composition consisting essentially of (i) 0.1 to 10% by weight of an isothiazolone compound selected from the group consisting of a compound of the following formula [1] and a compound of the following formula [2], (ii) 0.1 to 20% by weight of the aminocarboxylic acid of the following formula [3], and (iii) 0 to 50% by weight of a corrosion inhibitor, 0 to 50% by weight of a scale inhibitor, 0 to 30% by weight of an antimicrobial agent other than an isothiazolone compound, 0 to 10% by weight of a defoaming agent, 0 to 10% by weight of a surfactant, 0 to 10% by weight of an algicide and 30 to 99% by weight of water or a hydrophilic organic solvent;

[1]

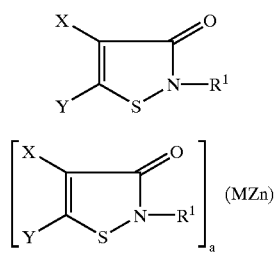

[2]

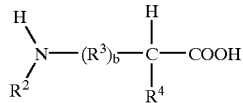

wherein $R^1$ represents a hydrogen atom, an alkyl group, an alkenyl group, an alkynyl group or an aralkyl group, X and Y each represents a hydrogen atom or a halogen atom or form a benzene ring in combination with carbon atoms at the 4- and 5-positions of the isothiazolone compound, M represents a cation of an alkali metal, an alkaline earth metal, a heavy metal or an amine, Z represents an anion forming, in combination with the cation represented by M, a compound having a sufficient solubility to form a complex compound, a represents 1 or 2 and n represents an integer required for the anion represented by Z to satisfy a valence of the cation represented by M;

[3]

$$\begin{array}{c} H \\ \diagdown \\ N \end{array} \!\!-\!\! (R^3)_b \!\!-\!\! \begin{array}{c} H \\ | \\ C \\ | \\ R^4 \end{array} \!\!-\!\! COOH$$

$R^2$ wherein $R^2$ represents a hydrogen atom or an alkyl group having 1 to 5 carbon atoms unsubstituted or substituted with a carboxyl group, $R^3$ represents a linear or branched alkylene group having 1 to 5 carbon atoms, $R^4$ represents a hydrogen atom or an alkyl group having 1 to 5 carbon atoms unsubstituted or substituted with a carboxyl group, a carbamoyl group, a hydroxyl group, a phenyl group, a hydrophenyl group, an ureido group, a methylthio group or a 4-imidazolyl group, $R^2$ and $R^4$ form a heterocyclic group unsubstituted or substituted with a hydroxyl group or an oxo group in combination with N—$(R^3)_b$—C and b represents 0 or 1.

* * * * *

UNITED STATES PATENT AND TRADEMARK OFFICE
CERTIFICATE OF CORRECTION

PATENT NO.    : 6,429,220 B1
DATED         : August 6, 2002
INVENTOR(S)   : Minoru Yagi et al.

It is certified that error appears in the above-identified patent and that said Letters Patent is hereby corrected as shown below:

Title page,
Item [56], FOREIGN PATENT DOCUMENTS, insert
-- JP   3-178969    8/1991
   JP   52-87230    7/1977
   WO   91/07090    3/1991
   EP   787430      8/1997 --.

Column 17,
Line 63, replace "at" with -- 0.8% --.

Signed and Sealed this

Ninth Day of September, 2003

JAMES E. ROGAN
*Director of the United States Patent and Trademark Office*